United States Patent [19]

Mutschler et al.

[11] Patent Number: 4,702,595
[45] Date of Patent: Oct. 27, 1987

[54] PATTERN RECOGNITION SYSTEM WITH WORKING AREA DETECTION

[75] Inventors: Carl E. Mutschler, Warminster; Mark E. Warner, Stowe, both of Pa.

[73] Assignee: SmithKline Beckman Corporation, Philadelphia, Pa.

[21] Appl. No.: 519,883

[22] Filed: Aug. 3, 1983

Related U.S. Application Data

[63] Continuation of Ser. No. 197,296, Oct. 15, 1980, abandoned.

[51] Int. Cl.[4] .................... G01N 33/48; G06K 9/20
[52] U.S. Cl. .................................... 356/39; 364/416; 377/10; 377/17; 382/6; 382/18; 382/48
[58] Field of Search ............... 356/39; 377/10, 17; 382/6, 18, 48

[56] References Cited

U.S. PATENT DOCUMENTS

| | | | |
|---|---|---|---|
| 4,000,417 | 12/1976 | Adkisson et al. | 235/92 PC |
| 4,015,108 | 3/1977 | Morton | 235/92 PC |
| 4,045,655 | 8/1977 | Suzuki et al. | 364/416 |
| 4,045,772 | 8/1977 | Bouton et al. | 235/92 PC |
| 4,097,845 | 6/1978 | Bacus | 356/39 |
| 4,175,859 | 11/1979 | Hashizume et al. | 364/416 |
| 4,362,386 | 12/1982 | Matsushita et al. | 356/39 |

Primary Examiner—Vincent P. McGraw
Attorney, Agent, or Firm—Caesar, Rivise, Bernstein, Cohen & Pokotilow

[57] ABSTRACT

A pattern recognition system is disclosed with working area detection which automatically positions a field in a proper position with respect to an optical scanning means to optimize the pattern recognition and to automatically enable examination of the field in a good working area. The system has particular application to the examination of blood smears on a slide by enabling the positioning of the slide to enable examination of the blood smear in a good working area without operator intervention.

17 Claims, 8 Drawing Figures

PERIMETER MASK

PATTERN RECOGNITION SYSTEM WITH WORKING AREA DETECTION

This application is a continuation of application Ser. No. 197,296, filed Oct. 15, 1980, now abandoned.

This invention relates generally to pattern recognition systems for use in automatic blood cell differential analyzers and more particularly to a pattern recognition system with working area detection to further automate the process of automatic blood cell recognition.

In the pattern recognition field, as it applies to the use of pattern recognition techniques for recognizing red blood cells and white blood cells in a wedge smear, the placement of the wedge smear with respect to the optical scanning system in order to permit the pattern recognition to be started is a function that must be performed by a skilled operator. In this respect, unless the operator is amply trained, it is difficult for the operator to determine where the optical scanner should be located with respect to the wedge smear to start the process of recognizing the white blood cells in the location of the scanner and immediately adjacent areas of the wedge smear.

For example, in optical pattern recognition systems which are utilized for the purpose of providing a differential white cell count of the blood of a patient, a sample of the whole blood is smeared and dried on a slide and a stain is used to enhance the contrast. In order to make an automatic differential white cell count of the blood, the slide is then placed on the stage of a microscope lens assembly which is a portion of a flying spot scanner and the operator must then examine the wedge smear in order to find the optimum working area of the slide.

The operator then examines the wedge smear to find a portion of the wedge smear in which approximately 50% of the red cells are touching. In those portions of the wedge smear where there is a higher percentage of blood cells touching the difficulty of recognition of the red blood cells is increased.

In those portions where there are less than 20% of the red blood cells touching, there are usually not enough white cells in order to obtain an examination of the requisite number of white blood cells to give a white blood cell differential count.

Because of the variability of wedge smears, the lengths of good working areas on different slides is variable and there are often tough decisions to be made by the operator at the time that the wedge smear is examined as to where to start the scanning of the smear for determining the white blood cell differential count.

It is therefore an object of this invention to overcome the problems experienced in the prior art.

Another object of the invention is to provide an automatic working area detection system for use in automatic blood cell differentiating devices.

Still another object of the invention is to provide a new and improved pattern recognition system with working area detection which enables the optimum portion of a working area to be examined at the start of the pattern recognition.

Another object of the invention is to provide a new and improved working area detection system which facilitates the finding of the optimum working area in a wedge smear.

Yet another object of the invention is to provide a new and improved working area detection system which utilizes the red blood cell morphology for determining the optimum working area in a wedge smear.

Still another object of the invention is to provide a new and improved system for determining the best working area in a blood smear which utilizes perimeter and area detectors.

These and other objects of the invention are achieved by providing a new and improved pattern recognition system for examining fields, means for positioning the field to enable examination of the field in a good working area. The system includes scanning means for scanning a field, platform moving means for moving the field with respect to the scanning means to move the position of the field scanned, and detection means responsive to the scanning means for determining when the field scanned is in a good working area. The platform moving means is responsive to the detection means for moving the platform so that the first field scanned in the cell classification mode is in a good working area of the smear.

This invention has particular application to pattern recognition systems for examining blood smears wherein the good working area is determined to be an area of the slide in which there is a predetermined distribution of red blood cell in the wedge smear.

In the preferred embodiment, the good working area of the wedge smear on the slide is determined by analyzing the red cell data obtained by optically scanning the wedge smear. This in turn enables a determination of the starting point for performing the white blood cell differential count and analysis of the red blood cell morphology on the slide.

The working area is found by placing the slide under the microscope and positioned at a fixed location with a preferably thick area of the smear in the optical axis of the scanning system. A coarse and fine focus operation is then performed.

After fine focus has been obtained, the wedge smear is scanned by the optical scanner and the data generated by the optical scanner is provided to the main shift register and used to obrtain measurements of the total area in the field scanned covered by red blood cells and the total length of perimeters of the red blood cells which are not overlapping other red blood cells.

The slide is then moved 400 microns towards the thin area of the smear and another analysis of the data generated by the optical scanner is made to again obtain measurements of the total area covered by the red blood cells and the total perimeter of the red blood cells in the field scanned.

During each examination of a field the area measurement is divided by the perimeter and multipled by a factor of (19/5). It has been found that by using this calculation or ratio a result of 33 or less represents a good working area in the blood smear is found.

Each time a ratio of 33 or less is found it is stored and when 20 consecutive fields containing a good working area are found an optimum area to start the search and classification scanning operation has been located. If 20 consecutive fields are not found having a good working area the scanning continues until the end of the wedge smear is reached.

The starting point at which the wedge smear is scanned for the purposes of classification of the blood cell is determined by the circuitry in accordance with the length of the longest string of consecutive fields scanned having a good working area.

If the slide is initially positioned in a location with respect to the optical axis of the optical scanning means which is too close to the good working area, the direction of movement of the slide is reversed until a thicker area of the smear is located along the optical axis of the optical scanner.

In the event 20 consecutive fields along the longitudinal axis of the slide cannot be found in which there is a good working area, the working area can be selected by other criteria.

Where the number of consecutive fields having a good working area is less than 20 and the position of the largest string of consecutive fields found is greater than 6 millimeters from the end of the blood smear, the blood smear is examined where the largest string of consecutive fields with a good working area is found.

Where the position of the largest string of consecutive fields with a good working area is found to be within 6 millimeters of the end of the blood smear, the slide is moved so that the optical axis of the scanning system is moved to a position 6 millimeters from the end of the smear to begin the classification scanning in a direction opposite to normal.

Where the work area scans have produced no fields with a good working area, the optical axis of the scanning means is located 6 millimeters from the end of the smear and the classification scanning started in a direction opposite to normal.

These and other objects of the invention can be readily appreciated as the same becomes better understood by reference to the following detailed description when considered in connection with the accompanying drawings wherein.

PATTERN RECOGNITION SYSTEM WITH WORKING AREA DETECTION

Figure 1:
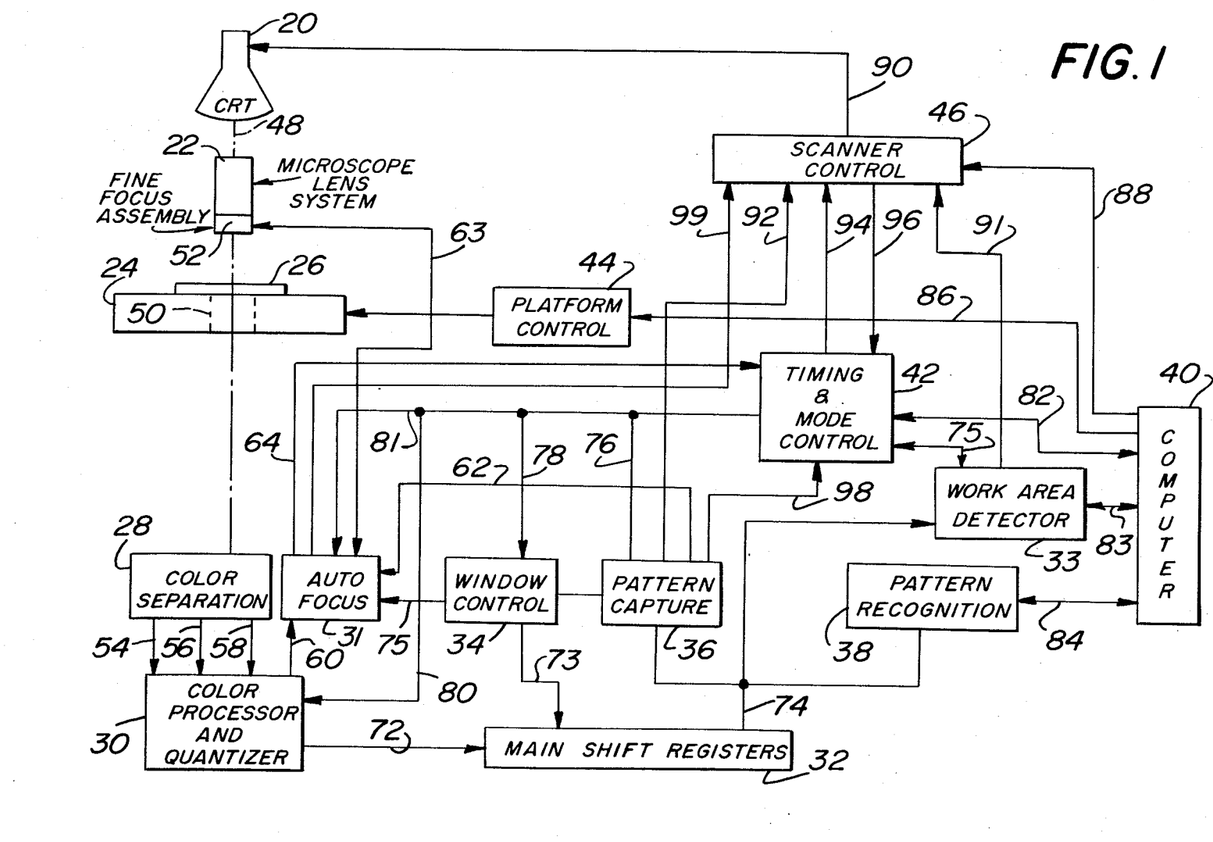
FIG. 1 is a schematic block diagram of a pattern recognition system embodying the invention.

Referring now in greater detail to the various figures of the drawing wherein like reference numerals refer to like parts, a pattern recognition system with working area detection embodying the invention is shown generally in FIG. 1. The preferred embodiment of the pattern recognition system with working area detection has particular application in a pattern recognition system having a scanning system for location and classification of patterns which is the subject of U.S. Pat. No. 3,873,974 issued on Mar. 25, 1975 to the assignee herein and in a pattern recognition system including automatic focusing, such as that shown in U.S. Pat. No. 4,012,634 issued on Mar. 15, 1977 to the assignee herein, the disclosures of which are incorporated by reference herein..

The pattern recognition system in FIG. 1 is adapted to provide a differential white blood cell count from a whole blood smear and to provide data relating to red blood cell morphology. The system includes a flying spot scanner optical system which includes a cathode ray tube 20, a microscope lens system 22, a platform 24 for supporting a glass slide 26 having a whole blood smear thereon, a light component separator 28, a color processor and quantizer 30, automatic focus circuits 31, a main shift register 32, a work area detector 33, a window control 34, a pattern capture 36, pattern recognition circuitry 38, a computer 40, timing and mode control 42, platform control 44 and scanner control 46. The cathode ray tube (CRT) 20 and the microscope lens system 22 are preferably mounted within a housing which is light sealed so that a beam of light 48 can be directed through the microscopic lens system for focusing on slide 26. Similarly, the platform 24 and the light component separator 28 are also encased in a housing to prevent light, other than the beam of light 48, from entering the light component separator 28. The platform 24 includes an opening 50 through which the beam 48 is directed to the light component separator.

Microscopic lens system 22 includes a fine focus assembly 52 to facilitate the automatic focusing. The fine focus assembly 52 is the subject of U.S. Pat. No. 3,915,560 issued on Oct. 28, 1975 to the assignee herein. The disclosure in said U.S. Pat. No. 3,915,560 is incorproated by reference herein.

The beam of light 48 is produced by the cathode ray tube 20 which provides the beam in a scan raster on the face of the cathode ray tube which is directed and focused by the microscope lens system down to a field of the size approximately 300 microns in length by 16 microns to 300 microns in accordance with the mode of operation of the pattern recognition system. That is, there are at least the following modes of operation in the pattern recognition system: the focusing mode at which time the lens system is automatically focused upon the surface of the slide on the stage of the microscope assembly, the work area detection mode, the pattern capture mode and the pattern classification mode.

During the focusing mode the beam on the scan raster on the face of the cathode ray tube is approximately 3"×3" and is reduced to a field the size of approximately 300 microns×300 microns. This is also the case in the pattern capture and classification mode. In the pattern capture mode the density of longitudinally extending beams is reduced to speed the capture of a pattern. In the work area detection mode the scan raster is directed and focused by the microscope lens system down to a field of the size of approximately 300 microns×16 microns. The density of the sampling in both the fast (longitudinal) direction and the slow (transverse) direction is approximately four samples per micron which is the same density of sampling that is used in the pattern classification mode.

The light passing through the slide 26 is directed to the light component separator 28 which filters the incoming beam and provides light through three spectral channels. The red, green and blue channels are chosen in accordance with the spectral absorbence of the component dyes in the Wright Stain which is conventionally used on a whole blood smear to facilitate visibility of the blood cells therein.

The light component separator 28 and the color processor and quantizer are the subjects of U.S. Pat. No. 3,827,804 issued on Aug. 6, 1974 to the assignee herein for Color Separation for Discrimination in Pattern Recognition Systems. The disclosure in said U.S. Pat. No. 3,827,804 is incorporated by reference herein.

The light beam 48 which passes through the blood smear on glass slide 26 enters the light component separator 28. Dichroic mirrors are provided for splitting the light into blue, red and green components of the light spectrum. Photomultipliers are provided which are responsive to each of the light components. The three photomultipliers convert the three light components (blue, red and green) into electrical signals which are generated on lines 54, 56 and 58 which are connected to the color processor and quantizer 30. Each of the signals corresponds to the color density of the light spectrum which the particular photomultiplier is responsive. The color processor and quantizer 30 preprocesses the signals on lines 54, 56 and 58 and quantizes the signals for providing the signals in binary form to the main shift registers 32, as well as to the automatic focusing circuitry 31.

The automatic focus circuitry 31 is responsive to the quantized signals received on lines 60 from the color processor and quantizer 30. The automatic focus system is initiated after a white cell has been captured within the field of view of the microscopic lens system. The signals indicating a capture are provided on lines 62 from pattern capture 36 to automatic focus 31. The automatic focus system is connected via line 63 to the fine focus assembly for automatically focusing the lens system prior to the work area detection and pattern capture. The automatic focus system also provides signals to the timing and mode control 42 via lines 64.

Window control unit 34 provides shift pulses a line 72 to the main shift register 32. The data received by main shift register 32 and automatic focus circuitry 31 from the color processor and quantizer 30 is determined by window control 34 which is connected to the main shift register via line 73 and automatic focus circuitry via line 75.

The work area detector 33, the pattern capture unit 36 and the pattern recognition unit 38 are connected to the output of the main shift register via lines 74. The timing and mode control 42 is connected via lines 75, 76, 78, 80 and 81 to the work area detector, pattern capture unit, the window control unit, the color processor and quantizer 30 and the automatic focus 31, respectively. The mode control selects the modes of operation. In a first mode a coarse focus is made in which the scanner quickly traverses a field in the blood smear and the platform is adjusted to bring the red cells into coarse focus. In a second mode of operation a blood cell is re-examined more closely. It is during the second mode that the automatic focus is initiated on red cells and prior to working area detection and then classification. The mode control enables the work area detection mode in which the optimum area of the blood smear is found for close examination. The timing and mode control is also connected via lines 82 to the computer 40. Computer 40 is connected via lines 83 to the work area detector 33, via lines 84 to the pattern recognition unit and to the platform 44 via lines 86 and to the scanner control 46 via lines 88.

The scanner control 46 is connected via lines 90 to the CRT and is also connected to the output line 91 of work area detector 33 and to the output line 92 of the pattern capture unit 36. The platform control 44 is mechanically connected to the platform 24 and moves the platform 24 in accordance with the signals received from the computer. During a searching mode, such as the work area detection mode and the pattern capture mode, the platform is moved in a predetermined sequence after each field has been completely examined. After a work area has been detected and close examination of the smear proceeds for classification, the platform control moves the platform 24 after a 300 micron × 300 micron field has been completely examined for details.

The platform control includes a stepping motor for moving the platform 24 in a predetermined pattern in both a longitudinal and transverse direction relative to the slide to assure that a separate and distinct field is viewed in each of the succeeding scans of the slide 26. The recycling of the beam 48 is controlled by the scanner control 46 which is connected to the timing and mode control 42 via lines 94 and 96. The pattern capture is connected via line 98 to the mode control 42. The pattern capture is connected via line 98 to the mode control 42. The mode control portion of the timing and mode control unit 42 causes the scanner control to operate the CRT in accordance with the mode that the system is operating. The automatic focus is connected to the scanner control by line 99.

Figure 2:
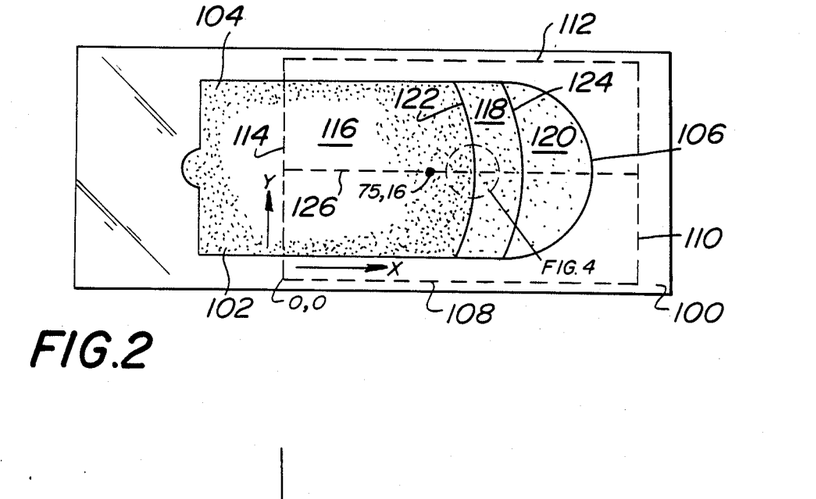
FIG. 2 is a top plan view of an idealized wedge smear on a glass slide.

A slide having an idealized representation of a blood smear thereon is shown in FIG. 2. The slide 100 is preferably a glass slide upon which smear 102 is preferably applied by an automatic blood smear device of the type shown in U.S. Pat. No. 3,880,111 issued on Apr. 29, 1975 to the assignee herein so that there will be substantial uniformity from one slide to another.

The blood smear 102 has its highest density of blood cells at the portion 104 of the blood smear and the density of the blood smear diminishes as the blood smear proceeds towards the end 106 of the blood smear.

The broken lines 108, 110, 112 and 114 form a rectangle which represents the area of the slide 100 that is brought under the optical axis of the scanning means of the system. That is, the extent of transverse and longitudinal movement of the slide with respect to the optical axis is confined within the broken lines 108 through 114. For ease of reference, the junction between lines 108 and 114 is referenced as 0,0 or the origin of both the X and Y axes of the X and Y directions of movement of the slide with respect to the optical axis. The X and Y axes proceed in the directions indicated by the arrows in FIG. 2.

The blood smear 104 is essentially inclusive of three areas. A first area 116 is an area which is densely populated by red blood cells and white blood cells. A second area 118, which is considered the good working area, includes a density of red cells which is between 50% and 20% of the red blood cells touching each other. A third working area 120 includes too low a density of red blood cells. A solid line 122 represents the general area of the blood smear wherein there is a density of blood cells that approximates 50% of the red cells touching and line 124 represents the area of the blood smear at which the density of red blood cells has decreased to a point that less than 20% of the red blood cells are touching each other.

There is also a broken line 126 shown in FIG. 2 which extends in the X direction along coordinate 16 in the Y direction. Each coordinate in both the X and Y directions is spaced 400 microns from the next adjacent coordinate.

During the examination of the smear for the good working area 118 of the blood smear, the slide is moved by the platform so that the optical axis of the scanning means proceeds along line 126.

Figure 3:
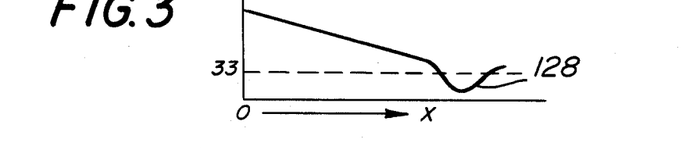
FIG. 3 is a diagrammatic graphical representation of the area/perimeter ratio along the length of a wedge smear.

FIG. 3 is a graphical representation of the area perimeter ratio along the X direction of the blood smear. That is, the X coordinate in FIG. 3 has been aligned longitudinally with the illustration of the slide in FIG. 2 so that it can be seen how the area perimeter ratio of the red blood cells varies along the length of the blood smear 102 along the line 126 shown in FIG. 2. The broken line in FIG. 3 which extends parallel to the X axis is provided on the coordinate 33 of the graph to represent a value of 33 along the area perimeter ratio coordinate axis. It can be seen that at the 0 coordinate along the X axis, the area perimeter ratio greatly exceeds 33. As the X coordinate increases towards the thinner density of the smear, the area perimeter ratio drops towards 33. It can be seen that the area perimeter ratio drops quickly to a value below 33 in the portion of the blood smear along the X axis adjacent the border 128 of the good working area 118. As the blood smear moves out of the good working area, the area to perimeter ratio again increases and rises above 33. Accordingly, the area perimeter ratio can be seen to be a powerful tool for the detection of the good working area. In FIG. 3, the portion 128 of the area perimeter ratio plot against distance moves below the numerical value 33 only in the good working area of the slide.

Figure 4:
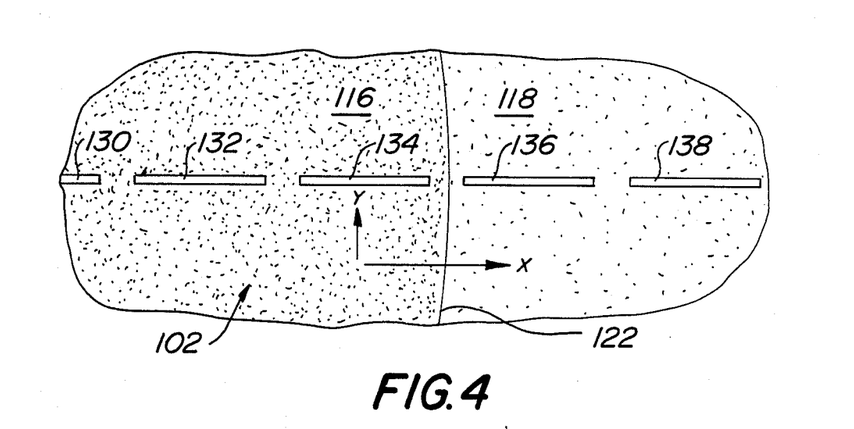
FIG. 4 is an enlarged fragmentary top plan view taken within the circle entitled FIG. 4 in FIG. 2.

FIG. 4 is an enlarged fragmentary portion of the area within the dotted line entitled FIG. 4 in FIG. 2. Superimposed over the portions of the dense portion 116 and the good working portion 118 of the blood smear 102 is a plurality of elongated rectangular boxes 130, 132, 134, 136 and 138. The rectangular boxes 130 through 138 each represent the working area scans which are 300 microns in the X direction and 16 microns in the Y direction.

As best seen in FIG. 2, the blood smear 102 contains a point labelled 75, 16 along line 126 which is superimposed over the blood smear and which represents the coordinates of the point at which the optical axis of the scanner is aligned with the slide when the slide is first placed on the platform and when work area detection is started. That is, the optical axis of the scanning system is disposed with respect to slide 100 at the point along the coordinate axis 75 is the X direction and 16 in the Y direction. Based on empirical data this is a position on the slide which is normally disposed in an area of a blood smear which contains a density of red blood cells which is more dense than the desired good working area 118 contains. Accordingly, the scan to detect the good working area is commenced at the location 75, 16 and is backed up (the optical axis moves to the left as seen in FIG. 2) if it turns out that the area perimeter ratio is too close to the good working area and proceeds in the upward direction (the optical axis moves to the right in FIG. 3) towards the end of the smear 106 when the area perimeter ratio is consistent with a dense portion of the smear.

Accordingly, the boxes 130 through 138 in FIG. 4 represent consecutive work area scans along the X direction. It should be noted that boxes 130, 132, 134, 136 and 138 represent scans taken at consecutive X coordinate positions, each position being spaced 400 microns. Thus the leftmost ends of scans 132 and 134 are spaced 400 microns apart.

Where the line 122 in FIG. 4 accurately represents a portion of the blood smear at which the good working area begins, the area perimeter ratio of the red blood cells examined in the area of the slide represented by box 134 are above 33 and the area perimeter ratio of the blood cells in the area 136 is 33 or lower.

The operation for finding the optimum working area therefore starts by loading a slide 100 in a predetermined position as slide 26 is shown in FIG. 1 on the platform 24. The position of the optical axis of the microscopic lens system with respect to the slide 100 is the coordinate 75, 16 shown in FIG. 2. The scanner is coarsely focused on the slide by looking at red cell data and positioning the platform about the Z axis (transverse to the plane of the slide) then performing a fine focus operation and then a working area scan is commenced.

As set forth above the coordinate position 75, 16 is normally disposed over a thick area of the smear.

The working area detector which is connected to the main shift registers 32 receives the data from the quantizer in the color processor and quantizer 30 relating to the color density of the area scanned at coordinate 75, 16. The data in shift registers 32 examined by detector 33 is the red blood cell information.

The work area detector, as will hereinafter be seen, includes an area detector and a perimeter detector. The area detector includes means for counting the number of sampling points found in the 300×16 micron area upon which a red blood cell is superimposed. The perimeter detector counts the number of points in the scanned area upon which there is detected the perimeter of the red blood cell.

It can be seen that the larger the density of the red blood cells, the higher the area perimeter ratio will be because the red blood cells overlap and therefore cover a greater portion of the scanned area and the number of points on the perimeters found is lower because only those portions of the perimeter of the red blood cell over a clear area are counted. Those portions of the red blood cell which are overlapping another red blood cell are not counted. In the good working area region, more of the red cells are separated and a pallor is introudced in the center of the red cell, which pallor does not register as a portion of the smear being covered by a red blood cell. Rather, the control pallor registers is seen as a background area. This pallor reduces the red blood cell area and increases the perimeter counts. However, at the very low density portion of the smear adjacent the end of the slide, the area perimeter ratio goes up again because central pallor is lost. In addition, the tendency of the red blood cells to be enlarged at the end of the smear adds area points faster than perimeter points.

After the area perimeter ratio is measured, during the first working area scanned, if the area perimeter ratio is 35 or less it indicates that the scan started too close to the good working area and therefore the platform is moved so that the scanner backs up along line 126 in FIG. 2 to a lower coordinate along the X axis. In the back-up mode, the platform is moved so that the slide is moved 4 units along the X direction with respect to the scanner before the next work area scan.

The scanner continues to be moved back with respect to the slide until an area perimeter ratio greater than 35 has been detected or the X coordinate on the slide of 63 is reached.

The slide is then moved by the platform so that the optical axis of the scanner moves upwardly in the X direction a step at a time, with a working area scan at each position. Each working area scanned is utilized for determining the area perimeter ratio of the red blood cells found with the field scanned.

The working area scans continue one step at a time until the end of the smear is reached or 20 consecutive fields are scanned in which the area perimeter ratio are found to have a value of 33 or less.

In the event that the working area detector does not find a string of 20 consecutive fields having an area to perimeter ratio of 33 or less, the largest string of fields found having an area to perimeter ratio of 33 or less is used to determine the starting point for classification scanning. The starting point is determined by the location and the length of the string.

If the good working area starts too close to the end of the smear, the slide is positioned so that the classification scanning begins 6 millimeters (mm) from the end of the smear and the search and classification mode proceeds by scanning the smear in the reverse direction proceeding from the 6 mm point from the end 106 of smear 102 towards the dense area 116 of the smear.

After the work area detector 33 determines where the good working area is located, the computer causes the platform control 44 to move the platform to a position within the good working area and then the search mode of the system is used to determine the location of patterns which are to be classified by the pattern recognition 38 and then fed to the computer 40. The scanner control 46 causes the CRT to generate a scanning raster which will be converted to the 300 micron × 300 micron scanning raster on the slide for use in capturing patterns and for classification.

Figure 5A:
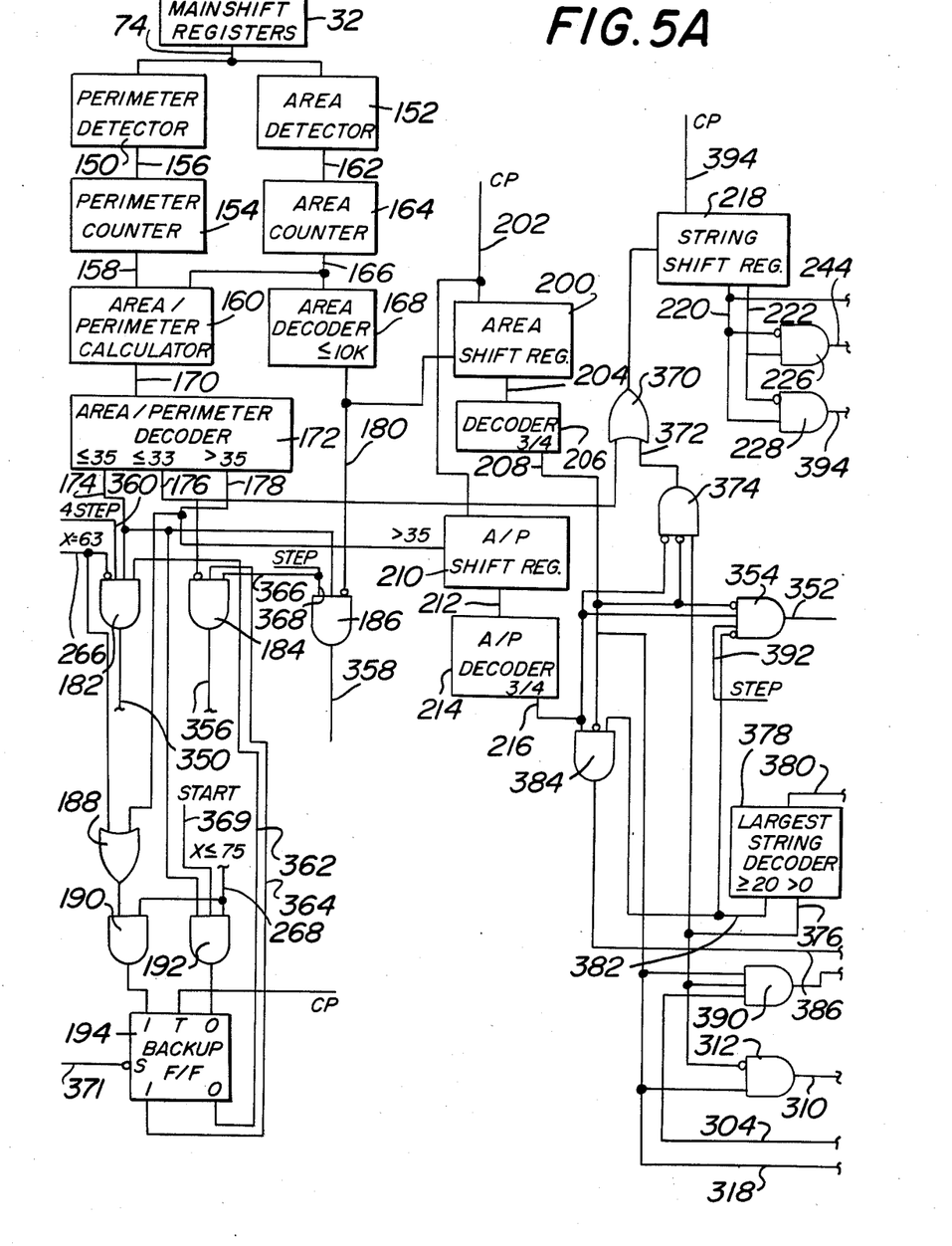
FIG. 5 is comprised of FIGS. 5a and 5b and is a schematic block diagram of the work area detector and associated control circuitry.
Figure 5B:
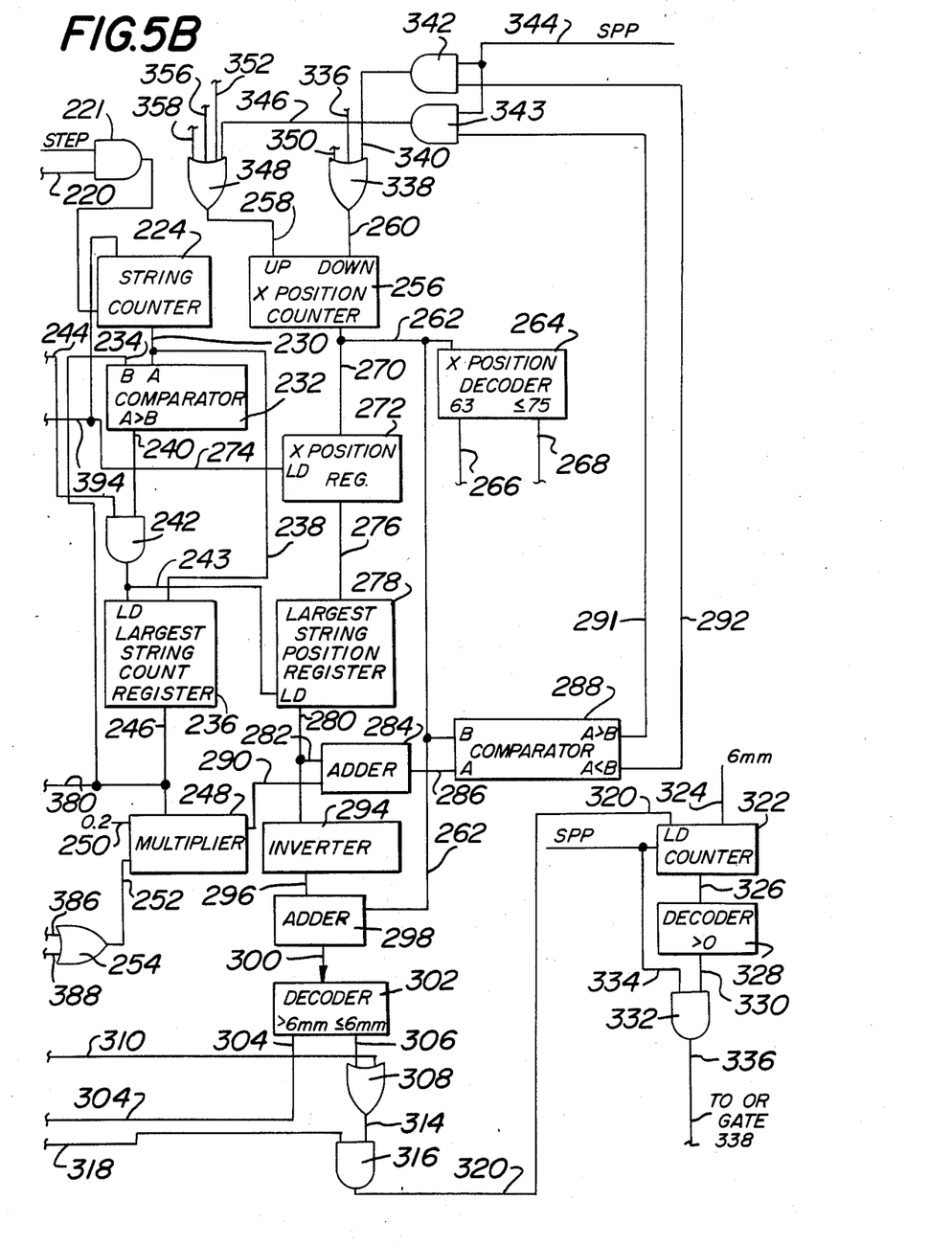

The work area detector and associated circuitry is shown schematically in greater detail in FIGS. 5a and 5b. It should be understood that the the logic shown in FIGS. 5a and 5b is preferably comprised of is a programmed microprocessor.

The work area detector includes a perimeter detector 150 and an area detector 152. The perimeter detector essentially detects each sampled position within a field that is on the periphery of red blood cell lying over a background area. The area detector 152 basically comprises a detector for determining whether a sampling point is disposed over a red cell. The perimeter detector 150 and the area detector are both connected to the output lines 74 of the main shift register 32.

The perimeter detector is essentially a mask which comprises a gate which is enabled when four to six of the nine input lines receive a 1.

Figure 7:
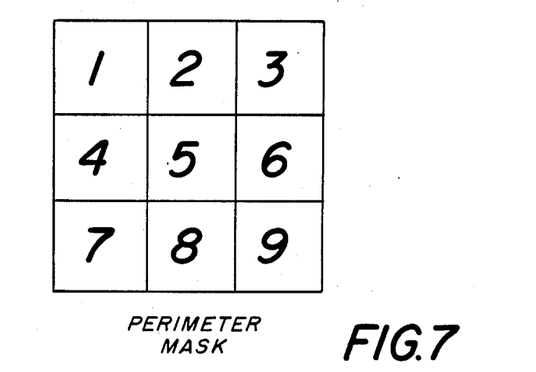
FIG. 7 is a diagrammatic representation of the perimeter gate used for determining the number of sampling points that fall on the perimeter of a red blood cell within a field scanned.

The perimeter mask is diagrammatically shown in FIG. 7. The perimeter mask in FIG. 7, as shown, represents the gate which is connected to the output line of the main shift register stages which correspond to a 3×3 sampling area of the field scanned. Thus, the blocks labelled 1, 2 and 3 on the top row of the perimeter mask represent three consecutive sampling points in a transverse direction within the scan that are immediately adjacent to each other and in the same row, whereas, blocks 1, 4 and 7 represent three immediately adjacent sampling points in a longitudinal column of point samples within the scanned area.

Each time a sampling point lies over a red blood cell a 1 is placed in the main shift registers. The output line from the shift register is a 1 at the time that the signal representative of the sampling point is disposed in the associated stage. Accordingly, the perimeter mask comprises a gate which includes nine input lines which are connected to the output of nine stages which are representative of nine immediately adjacent sampling points in the field. The gate is enabled each time four, five or six of the nine sampling points of the mask have a red cell located thereat. This represent a perimeter detection when four to six of the points lie on a red blood cell area and the other points lie in the background area.

The area detector 152 is a single point detector which is connected to a single output line to a single stage of the main shift register and is enabled each time a 1 is moved into the shift register stage.

In view of the fact that the scanned area during a working area scan is 300 microns × 16 microns and the sampling points are disposed four sampling points to a micron in each coordinate direction, the area detector 152 samples 76,800 points within the field scanned. Similarly, the perimeter detector 150 samples 76,800 points to determine whether they are on the perimeter of a red blood cell. As set forth above, a perimeter is not detected when a red blood cell is lying over another red blood cell at the point where one red blood cell is overlapping another. Rather, the perimeters will be picked up only at the points that the red blood cell is lying over plasma or background.

The perimeter detector 150 is connected to a perimeter counter 154 by line 156. Each time the perimeter mask is enabled, the perimeter detector 150 provides a signal on line 156 which is counted by the perimeter counter 154. The perimeter counter 154 basically comprises a binary counter which counts each pulse received on line 156. The counter includes an output line connected to each stage, which output lines 158 are connected to an area/perimeter calculator 160 via output lines 158. The area perimeter calculator 160 is a conventional calculator including a binary divider and multiplier.

The area detector 152 is connected via lines 162 to an area counter 164. Area counter 164 is also a binary counter which is stepped each time the area detector 152 detects a 1 in the stage of the shift register 32. The area detector then provides a triggering signal on line 162 which causes the area counter to be stepped. The area counter stages each include an output line which are connected to output lines 166 to the area perimeter calculator 160 and to an area decoder 168.

The area perimeter calculator 160 divides the count received from the area counter by the count received from the perimeter counter 154. This reasult is multiplied by the factor 19/5 to provide the area perimeter ratio. The binary output of the calculator 160 is then fed via output lines 170 of the calculator 160 to an area perimeter decoder 172. The area perimeter decoder comprises three conventional plural line binary input to single output line decoders. There are thus three output lines, 174, 176 and 178 which are enabled respectively when the area perimeter decoder receives from the calculator a result of 35 or less, 33 or less, more than 35.

Area decoder 168 is also a conventional plural line binary input decoder which has an output line 180 which receives a positive going signal each time the decoder determines that the count on lines 166 is equal to or less than 10,000 (10k).

Disclosed below the area perimeter decoder in FIG. 5a is the logic circuitry that is used for the movement of the platform for the successive work area scans to determine the portion of the smear which is a good working area. Provided below the area perimeter decoder 172 are AND gates 182, 184 and 186.

It should be noted that conventional logic terminology is used throughout. For example gate 182 is a conventional AND gate having four inputs. The leftmost input having a circle adjacent the input of the gate represents an inverted input which requires a zero on the input line in order to enable the gate 182 when 1's are provided on each of the three remaining inputs. Gates in the shape of gate 188 are OR gates which are enabled by a 1 on any of its input lines.

Also provided in addition to OR gate 188 are two AND gates 190 and 192 and a backup flip flop 194. The backup flip flop 194 is a conventional flip flop having a triggering input (T) which controls the state of the flip flop in accordance with the signals to the 1 and 0 inputs thereof. Thus, if a 1 is provided on the line to the 1 input, then at the time that the leading edge of a pulse is provided to the trigger input the flip flop will be set to the 1 state. Similarly, if a 1 is provided on the 0 input of the flip flop 194 at the time that a leading edge of a pulse is provided in the trigger input, the state of the flip flop will be set to 0. The S input enables the flip flop 194 to be preset to a 1 state at the beginning of a work area detection operation.

An area shift register 200 is provided which is comprised of a four stage binary shift register. The input to the area shift register is connected to the output line 180 of the area decoder 168. The shift input of the area shift register 200 is connected to an output line 202 of the timing control. The output lines of the four stages of the area shift register 200 are connected via lines 204 to a decoder 206 which is a three out of four line gate detector. That is, each time that any three or more of the four input lines to the decoder 206 are a 1, the decoder is enabled causing a high signal on output line 208.

The greater than 35 output line 178 of the area perimeter decoder 172 is connected to an A/P shift register 210. The A/P shift register comprises a four stage shift register, each having an output line which is connected via line 212 to an A/P shift register decoder 214. The decoder 214 is similar to decoder 206 in that when at least three out of four of the input lines to the decoder 214 are a 1, the decoder is enabled providing a high signal on output line 216.

A string shift register 218 is provided which comprises a two stage shift register which is used to determine the beginning and end of a string of consecutive fields containing a good work area. The string shift register includes two output lines, 220 and 222 which are connected to the outputs of the first and second stages, respectively, of the binary shift register 218.

The string shift register 218 is connected via output line 220 to the input of AND gate 221 and to the inverted input of AND gate 226 and an input of AND gate 228. The output line of AND gate 221 is connected to the step input of string counter 224 via line 219.

Output line 222 of string shift register 218 is connected to an input of AND gate 226 and to the inverted input of AND gate 228.

The string counter 224 is a conventional binary counter with the output of each stage of the string counter connected via output lines 230 to the A input of a binary comparator 232. The comparator 232 compares the binary counts provided on lines 230 and B input lines 234 which are connected to the output lines of a largest string count register 236.

The largest string count register 236 is a binary register, each stage of which has an input line connected via lines 238 to the ouput lines of the stages of string counter 224. The comparator 232 causes an output of 1 to be generated on output line 240 each time the input receives a higher number than the B input which means the count in the string counter 230 is higher than the count stored in the largest string count register 236.

Output line 240 is connected to an input of AND gate 242. The other input line 244 of AND gate 242 is connected to the output line of AND gate 226. THe output of each of the stages of the largest string count register 236 are connected via output lines 246 to a multiplier 248.

Multiplier 248 is a conventional binary multiplier which multiplies the binary signal provided on lines 246 by a factor of 0.2 which is provided in binary form to the input of multiplier 248 as a fixed factor on lines 250. The factor 0.2 is provided to lines 250 from the computer 40.

The multiplier 248 also has an enabling input 252 which requires a high signal thereon in order to enable the multiplication being performed by the multiplier 248. The line 252 is the outputof an OR gate 254.

The working area detector also includes an X position counter 256 which controls the position of the platform for movement of the slide with respect to the optical axis of the scanner. The X position counter 256 is a bi-directional binary counter which is stepped upwardly upon each pulse provided on the input line 258 and is stepped downwardly each time a pulse is received on line 260.

The output lines of each of the stages of the X position counter are connected via lines 262 to an X position decoder 264 which enables the determination of a count in the X position counter of 63 or 75 or less. X position decoder 264 comprises two plural input binary to single output decoders. The first decoder is set to provide a 1 on output line 266 when the signals on lines 262 represent the number 63 and the second decoder is set to provide a 1 on output line 268 when the signals on lines 262 represent a number of 75 or less.

The line 266 thus receives a high signal each time the counter of 63 is in the X position counter 256 and output line 268 receives a high signal each time the count in the X position counter 256 is 75 or less. The output of the X position counter stages are also connected via lines 270 to an X position register 272.

The X position register is a binary register which enables the count in the X position counter 256 to be loaded into the register each time the signal on input line 274 goes high. The output lines of the stages of the X position register are connected via output lines 276 to the largest string position register 278.

The largest string position register 278 is also a binary register which has a load input which is connected to the output line 243 of AND gate 242 and which stores the position of the largest string position in register 272 each time a new longest string is found.

The output lines of each of the stages of the largest string position register are connected via output lines 280 to the input 282 of adder 284. Adder 284 is a conventional binary adder which provides the sum of the binary numbers on lines 282 and 290 on output lines 286 to a comparator 288.

The input lines 290 to adder 284 are connected to the output lines of multiplier 248. Comparator 288 is a binary comparator having A and B inputs. The A input is connected to the output lines of adder 284 via lines 286 and the B input is connected to the output lines 262 of the X position counter 256. The comparator 288 has a first output line 291 which receives a high output signal each time the signals at input A represent a number higher than the signals at input B. The output line 292 is high when the signals at input A represent a number larger than that at input B.

The output lines 280 from the largest string position register 278 are also connected to the input of an inverter 294. The inverter 294 provides the compliment of the binary number provided on lines 280 to the output lines 296 which are connected to the input of an adder 298. The second input of adder 298 is connected to the output of X position counter 256 via lines 262.

Signals representative of the sum of the numbers represented by the signals on lines 296 and 262 are provided by the adder 298 on output lines 300 which are connected to a decoder 302. The decoder 302 comprises a pair of binary plural input to single output decoders. If the output signals from adder 298 represent a number of millimeters greater than 6mm then output line 304 of comparator 302 goes high. If the signals represent a number of millimeters which are 6 mm or less, then output line 306 goes high.

The output line 306 is connected to an input of an OR gate 308. The second input of OR gate 308 is connected via line 310 to the output of AND gate 312. The output of OR gate 308 is connected via output line 314 to the input of AND gate 316. The second input of AND gate 316 is connected via line 318 to the output line 208 of decoder 206.

The output of AND gate 316 is connected via output line 320 to the load input of a counter 322. The counter 322 is a binary counter which is preset in accordance with the binary signal on input lines 324 when a load signal is provided on input line 320. The output of each stage of counter 322 is connected via output lines 326 to the input of a decoder 328.

The decoder 328 preferably comprises an OR gate which produces a high signal on output line 330 as long as the signals on lines 326 represent a number greater than zero. The output line 330 is connected to the input of an AND gate 332. AND gate 332 further includes a second input line 334 which is connected to the output of the timing control and receives the SPP signals.

The AND gate 332 is connected to output line 336 to an input of OR gate 338. Input line 340 of OR gate 338 is connected to the output of AND gate 342. A first input line of AND gate 342 is connected to the output line 344 of the timing control and receives the SPP signal thereon. The output line 344 of the timing control is also connected to an input of AND gate 343. The second input of AND gate 342 is connected to the output line 292 of comparator 288. The second input of AND gate 343 is connected to the output line 291 of comparator 288. The output of AND gate 343 is connected via line 346 to an input of OR gate 348.

The third input of OR gate 338 is connected to output line 350 of AND gate 182 in FIG. 5a. Input line 352 of OR gate 348 is connected to the output of AND gate 354 in FIG. 5a. Input line 356 of OR gate 348 is connected to the output of AND gate 184 in FIG. 5a. Input line 358 of OR gate 348 is connected to the output line of AND gate 186 in FIG. 5a.

AND gate 182 has its inverted input connected via line 266 to the output line 266 of X position decoder 264 which goes high when the X position counter represents that the position of the optical axis with respect to the slide is 63 along the X axis. Input line 360 of AND gate 182 is connected to the output of the timing control and receives the 4 STEP signal. A third input of the AND gate 182 is connected via line 174 to the equal to or less than 35 output of the area perimeter decoder 172. The fourth input of the AND gate 182 is connected via line 362 to the zero output of the backup flip flop 194.

The inverted input of AND gate 184 is connected via line 176 to the equal to or less than 33 line of the area perimeter decoder 172. A second input of AND gate 184 is connected via line 364 to the 1 output line of the backup flip flop 194. A third input of AND gate 186 is connected via line 366 to the output of the timing control and receives the STEP signal. AND gate 186 has a first input line 368 which is connected to the output line of the timing control and receives the STEP signal. A second input to AND gate 186 is connected to output line 174 of the area perimeter decoder 172. The inverted input of AND gate 186 is connected to the output line 180 of the area decoder 168. The timing control is connected via line 202 to the trigger or shift input of the area shift register 200 and the A/P shift register 210.

OR gate 188 or a first input connected to output line 266 of the X position decoder 264. The second input of OR gate 188 is connected to output line 178 of area/perimeter decoder 172.

The output of OR gate 188 is connected to a first input of AND gate 190. The second input to AND gate 190 is connected to output line 268 of the X position decoder 264. The output of AND gate 190 is connected to the 1 input of flip flop 194. AND gate 192 has a first input connected to output line 174 of the area/perimeter decoder 172. A second input of AND gate 192 is connected via line 369 to the output of the timing control and receives the START signal. The third input of AND gate 192 is connected to output line 268 of the X position decoder 264. The output of AND gate 192 is connected to the zero input of backup flip flop 194. Backup flip flop 194 has its set input connected via line 371 to the timing control which sets the back up flip flop at the beginning of each work area detection cycle.

Output line 176 of the area perimeter decoder 172 is connected to a first input of OR gate 370. The remaining input of OR gate 370 is connected via line 372 to the output of an AND gate 374. The AND gate 374 has a first input which is connected to output line 216 of the A/P shift register decoder 214. The inverted input of AND gate 374 is connected to output line 208 from decoder 206 and a third input of AND gate 374 is connected via output line 376 of a largest string decoder 378.

The largest string decoder 378 is a pair of binary plural input to single output line decoders which are connected at their inputs to lines 380 which are connected to the output lines 246 of the largest string count register 236. The largest string decoder has two output lines 376 and 382. Provided on output line 376 is a high signal each time that the count in the largest string count register is greater than zero. The output line 382 is high whenever the count in the largest string count register is equal to or greater than 20.

The output line 322 of largest string decoder 378 is connected to an input of AND gate 384. The inverter input of AND gate 384 is connected to output line 208 of decoder 206. A third input of AND gate 384 is connected to the output line 216 of A/P decoder 214. The output of AND gate 384 is connected via line 386 to an input of OR gate 254. The second input 388 of OR gate 254 is connected to the output of AND gate 390. A first input of AND gate 390 is connected to output line 208 of decoder 206. A second input of AND gate 390 is connected to the output line 376 of the largest string decoder 378. A third input line of AND gate 390 is connected via line 304 to the output of comparator 302.

AND gate 354 has a first input which is connected to the output line 208 of decoder 206, a second input which is connected to the output line 216 of decoder 214, a third input line which is connected to the output of the timing control and receives the STEP signal. The inverted input to AND gate 354 is connected to output line 382 of the largest string decoder 378.

Figure 6:
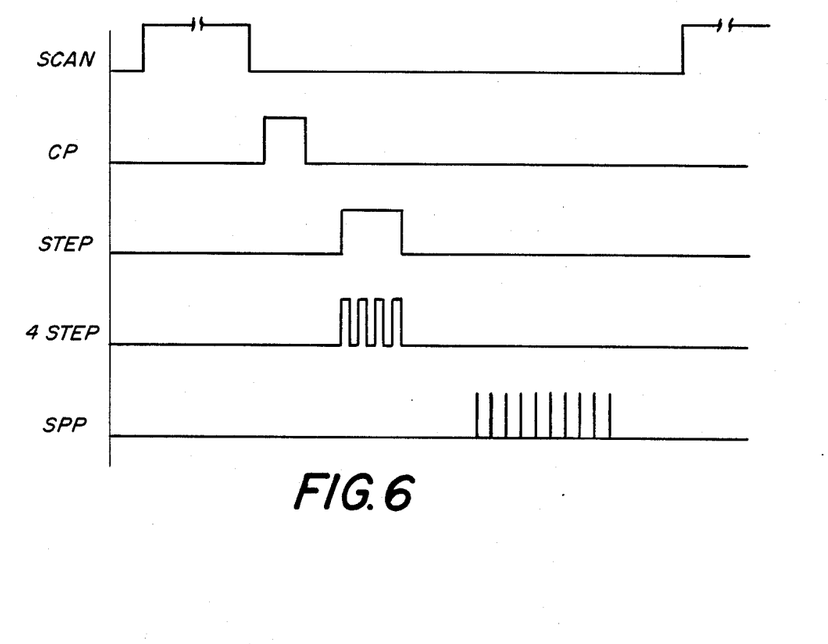
FIG. 6 is a graphic representation of the signals generated by the timing and mode control used in the circuitry shown in FIGS. 5a and 5b.

Referring now to FIG. 6, there is shown a graphical representation of several of the signals generated by the timing control which are used throughout the circuitry of FIGS. 5a and 5b. For purposes of clarity several timing signals and inputs which are used to reset the work area detector after each complete cycle are not shown.

On the first line of FIG. 6 there is shown the SCAN signal provided by the timing control to the scanner control 46 in FIG. 1. The scanner is in operation for the purpose of a work area scan when the signal goes high and such scanning is in the order of 32 milliseconds long. The period between each scan is approximately 108 milliseconds. During the first 8 milliseconds after a scan, than CP pulse is generated which causes analysis of the information which has been generated during the scanning cycle. That is, the area detector and perimeter detector are operable while the scan signal is high. After the work area scan has been completed, the analysis clock pulse CP is provided to the trigger input of the backup flip flop 494.

The backup flip flop 194 which is set to the 1 state during the first scan remains in the 1 state or is switched to the 0 state dpeending on the calculation made by the calculator 160 on the basis of the data found in the blood smear in the area scanned. That is, during the scanning the perimeter detector 150 and the area detector determine the number of points on the perimeter and the number of points covered by red blood cells, respectively. The count in perimeter counter 154 is fed to the area/perimeter calculator 160 as is the count from the area counter 164. The area perimeter calculator then provides the resulting area perimeter ratios on the lines 170. This area perimeter ratio is fed to the decoder 172 which determines whether the area perimeter ratio is greater than 35, smaller than or equal to 33 and/or smaller than or equal to 35.

Based on these determinations, the analysis clock enables the backup flip flip to remain in the 1 state or switched to a zero state and causes the signal from the area decoder 168 to be provided to the area shift register 200. The CP pulse also provides a signal on line 394 to be fed to the shift input of the string shift register 218 to place the signal on the output line of OR gate 370 in the string shift register so that it can be determined whether there is the beginning or the end of a string or whether a larger string has yet been determined. The CP signal also enables gate 221 when a 1 is inserted in the first stage of string shift register 218.

As seen in FIG. 6 after the CP goes low a STEP signal is generated by the timing control which is utilized for the purpose of stepping the X position counter up or down for the control of the movement of the platform for moving the slide with respect to the optical beam in accordance with the requirements of the work area detector.

There is also a 4 STEP pulse which is provided in the same period as the STEP pulse is provided except that four pulses are provided so that the X position counter can be stepped down by four counts during the peiod that the counter is stepped down. Finally, in the period between the end of the STEP and the 4 STEP pulses and the beginning of the next scan, there are approximately 100 milliseconds in which time start position pulses (SPP) are generated which cause the X position counter to be moved up or down in accordance with the position that the platform must be moved in order to enable the start of the scanning of the slide for the purpose of classification of the patterns on the slide. The SPP pulses are generated constantly through the 100 millisecond time period and only those pulses that are needed to step up the X position counter or step down the X position counter are used to move the platform.

The work area detector determines the position for scanning the slide when string counter 224 has reached a count of 20 or when the end of a smear is reached.

OPERATION OF WORK AREA DETECTOR

The first operation that is performed by the work area detector is to determine at the initial location of the slide with respect to the optical axis of the scanning system if it is an optimum position to start the working area scans. It will be remembered that the object of the placement of the optical axis of the scanner at the coordinate position 75,16 is to examine the normal slide in a portion of the smear which is more densly packed than is desired for a good working area.

This determination is made during the first working area scan by obtaining the number of perimeter points and the number of area points by the peirmeter detector and area detectors 150 and 152, respectively.

The area perimeter ratio is determined by the calculator 160 and the area/perimeter decoder 162 provides an output signal on the appropriate output lines in accordance with the area perimeter ratio determined by calculator 160.

If the optical axis of the scanning system is disposed over a field of red cells which is more dense than a good working area, the output line 178 goes high indicating that there is an area perimeter ratio of over 35. When the signal on line 178 goes high the OR gate 188 is enabled thereby providing a high signal at the first input of AND gate 190. Because the X coordinate of the slide with respect to the optical axis is 75 the input line to AND gate 190 which is connected to line 268 is also high thereby enabling AND gate 190 and the backup flip flop 194 to be set to one when the leading edge of the CP pulse is generated after the scan.

When the backup flip flop is set to the one state, it allows the AND gate 184 to be set to be enabled upon the application of the step pulse from the timing control which is applied via line 366 to AND gate 184. The third input of the AND gate 184 is enabled by the fact that line 176 from the decoder is low because the area perimeter ratio is more than 33 and line 176 is connected to an inverted input. When AND gate 184 is enabled during the STEP pulse, the output line 356 goes high and thereby enables OR gate 348 which generates a positive pulse on line 258 the step the X position counter up.

When the X position counter has been stepped up one it causes the platform to be moved so that the optical axis of the scanner is disposed at the coordinate position 76,16 of the slide. A working area scan is generated at each successive X coordinate position until either a string of 20 consecutive good working areas have been found or in the alternative the end of the blood smear is reached.

In order to continue stepping up the X position counter 256 even after the area perimeter ratio drops below 33, AND gate 186 provides stepping pulse via line 358 to OR gate 348 to the up position of the X position counter 256 when the area perimeter ratio is 35 of less and the end of a blood smear has not been reached as would be indicated by a high signal on output line 180 of the area decoder 168. That is, the signal on line 180 remains low until the area decoder 168 determines that less than 10,000 area counts have been found during a work area scanned. This indicates that a very thin area of the blood smear has been scanned. In the event that the portion of the blood smear scanned is a low density portion, but the end of the smear has not been reached, pulses to step the X position counter may also be provided by AND gate 354 which is enabled by the step pulse when a string of 20 consecutive good working areas has not been found, three out of the last four working areas has not caused a count of 10,000 or less, and three of the last four working areas have not been a good working area.

In the event that the starting position for the slide with respect to the optical axis is disposed with an area under the scanner which is too close to a good working area, the system operates in the following manner. During the scanning operation the perimeter detector and area detector determine the number of perimeter points and area points which satisfy the respective masks in the detectors 150 and 152. At the end of the scan the perimeter counter 154 and area counter 164 provide to the area perimeter calculator 160 the totals found during the scan.

The decoder 172 then produces a high signal on line 174 which indicates that an area perimeter ratio of 35 or less has been found and therefore provides an enabling signal to AND gate 192. The line 268 is also high because the X coordinate is 75, AND gate 192 is therefore enabled causing a high signal to be provided at the 0 input of the backup flip flop 194. Accordingly, when the CP pulse is generated the leading edge causes the backup flip flop switch go to 0 zero state and causes AND gate 182 to be set to be enabled by the 4 STEP pulses when generated by the timing control on line 360. Because the X coordinate is not 63, but rather 75, the signal on line 266 to the inverted input of AND gate 182 is low. As set forth above the signal on line 174 is high, thereby requiring only the pulses on the four step line 360 to cause enablement of the gate 182. Since the signal provides four step pulses on line 360 the AND gate is enabled four times, there are four pulses generated on line 350 from the output of AND gate 182 which are transmitted to the OR gate 338 and causes four pulses to be provided to the down input of the X position counter 256. These four pulses cause the X position counter to be stepped down four positions to cause the count in the X position counter to be changed to 71.

The X position counter having been decremented causes the platform to be moved so that that optical axis of the scanner is then moved to the coordinate position 71,16 of the slide and a working area scan is then performed on the slide at that coordinate position.

If the area perimeter ratio found during the second scan is greater than 35 then the backup flip flop 134 is set to the 1 state and thereby causes the X position counter 256 to be incremented again by 1 at the time that the step pulse is generated by the timing control. In this case, the X position counter is incremented after each working area scan.

If the X counter is moved to coordinate 71 along the X axis and the area perimeter ratio in the area scanned is again equal to or less than 35, the AND gate 182 is again enabled causing four pulses to be provided to the down input of X position counter 256 via OR gate 338 and thereby causes the X position counter to be stepped down to the count of 67. The platform is then moved to the position that the optical axis is disposed at the position x equals 67 along the coordinate axis. If the area perimeter ratio of the red blood scanned in the area disposed at the X equals 67 coordinate position is again less than 35 or less, it causes the X position counter to again be stepped down four counts which causes the platform to again be moved causing the slide to have the optical axis disposed at the coordinate position X equals 63.

When the X equals 63 coordinate is reached, input line 266 to the AND gate 182 goes high thereby causing the AND gate 182 to be disabled. However, OR gate 188 is enabled causing AND gate 190 to be enabled because the coordinate position along the X axis is equal to 63. Backup flip flop 194 is then reset to the one state upon the leading edge of the next CP pulse. Accordingly, it can be seen that backup flip flop causes the optical axis of the scanning area to be moved towards the more dense area of the slide until either an area perimeter ratio of over 35 is reached or the X coordinate of 63 is reached.

In either event once the backup flip flop is set to the 1 state the working scans are generated at each coordinate position consecutively along the length of the smear until the end of the smear is reached or 20 consecutive good working areas have been scanned.

During each work area scan, an area perimeter ratio is calculated by calculator 160 which is provided to the decoder 172 and provides signals on the appropriate lines 174, 176 and 178. Each time that the scanned area shows an area to perimeter ratio of 35 or less, a high signal is provided on line 174. Each time the area to perimeter ratio is 33 or less a high signal is generated on line 176. Each time the area to perimeter ratio is found to be over 35 a high signal is provided on output line 178.

Each time a signal is generated that is high on line 176 it represents a good working area has been found in the smear. Thus, after a work area has been scanned and line 176 goes high, OR gate 370 is enabled thereby providing a 1 at the input of string shift register 218 which is stored upon receipt of the leading edges of the CP pulse.

AND gate 228 which is connected to the output of the string shift register 218 detects the first good work area stored in the shift register. That is, as the first stage of the shift register is changed to the 1 state, line 220 goes high, thereby causing the AND gate 228 to be enabled. The signal on line 394 causes the string counter to be cleared on the leading edge of the pulse. Each time a 1 is placed in shift register 218, string counter 224 is stepped during the STEP pulse which enables AND gate 221. Counter 224 is thus stepped up one for each working area scanned in which the blood cell area perimeter ratio is 33 or less.

It should also be noted that the input to the string shift register is connected to the output of an OR gate 370. Not only does the string shift register store consecutive ones as a result of an area perimeter ratio being 33 or less, but there is also a provision for allowing for minor variations and faults in the smear once a good working area has been found. Thus, the OR gate 370 is enabled if the area perimeter ratio is more than 33 if AND gate 374 is enabled.

AND gate 374 is enabled only after a string of good wong areas has been started as indicated by the high signal on the output line 376 of the largest string decoder 378. If at least one good working area has been found the string decoder has a high signal on the output line 376.

The second input to AND gate 374 is from output line 208 of decoder 206. The output line of decoder 206 is high only when three out of four of the work areas scanned had a count of 10,000 or less. This condition is considered to be the end of the blood smear.

Thus, when three out of four consecutive working area scans are over fields in which less than 10,000 red cell counts are found the high signal on line 208 indicates that the scanner has reached the end of a blood smear. When the decoder 206 provides a low signal on line 208 it is indicative of the end of the blood smear not having been reached. Such a low signal is required to enable AND gate 374. The third condition for enabling AND gate 374 is that at least two out of the four last consecutive working area scans be close to a good working area. When three out of the four last working area scans have an area perimeter ratio of more than 35, line 216 goes high. However, if at least two of the fields had an area perimeter ratio of 35 or less there is a low signal generated on the output line 216 which causes gate 374 to be enabled and provides a 1 to the string shift register even though a minor variation may have caused the last area scanned to produce an area to perimeter ratio of more than 33.

At the time that the AND gate 228 is enabled at the beginning of a string it also causes the X position register 272 to have loaded therein the position of the scanner which is indicated by the count in the X position counter 256 at which the first good working area is found.

Each work area scan causes the X position counter 256 to be stepped up and thereby causes the next working area scanned to be at the next consecutive X location along the field of the blood smear.

For each consecutive working area scanned in which the area perimeter ratio is found to be 33 or less a 1 is inserted into shift register 218 and the string counter 224 incremented by 1. As soon as a working area scan produces an area perimeter ratio of 34 or more and the AND gate 374 is not enabled, a zero is inserted into the string shift register. The insertion of a 0 into the first stage of the string shift register 218 in combination with the 1 in the second stage causes AND gate 226 to be enabled, thereby providing a high signal on line 244 which indicates that an end of the string has been reached. The end of the string indication in the form of a high signal on line 24 allows AND gate 242 to be enabled if the count in string counter 224 is higher than the previous largest string count stored in string count register 236.

Since the string of good working areas was the first good working area string encountered, the string counter 224 has a greater count than the largest string count register 236 because the largest string counter register is reset after each good working area detection has been made. Therefore when the first string ends, the count in register 236 is zero. Accordingly, AND gate 242 is enabled causing a sigal to be provided on output line 243 of AND gate.242 which causes a loading signal in the largest string count register 236 which permits storage of the count in counter 224 via lines 238.

The output line 243 of AND gate 242 also causes a loading into the largest string position register of the position of the X register at the position where the string was started.

If the string count placed in the largest string count register 236 is 20 or greater, the largest string decoder 378 causes a signal on output line 382 to go high which causes AND gate 384 to be enabled and thus produce a high signal on line 386 which enables OR gate 254. The enabling of OR gate 254 in turn causes the multiplier 248 to be enabled to multiply the count found in the largest string count register times 0.2. The output product from multiplier 248 is provided on output lines 290 to the adder 284 which is added to the count found in the largest string position register 278. The sum produced on output lines 286 is thus the position of the first field in which the string of 20 or greater was found, plus 0.2 times the number of consecutive fields of good working area. This sum on line 286 represents the position that the X position counter is set in order to start the classification and search scanning modes of operation. The slide is then disposed with the optical beam at the X position represented by the signals on line 286. This is accomplished by comparator 288 which compares the sum on lines 286 with the present count found in the X position counter 256.

The sum on lines 286 is smaller than the count found in the X position count when a string of 20 or greater has been found. Accordingly, the output line 292 goes high thereby enabling AND gate 342 each time an SPP pulse is generated by the timing control. The X position counter is thus stepped down until such time as the count in the X position counter is equal to the sum on lines 286 from adder 284. As soon as the numbers provided on lines 286 and 262 to the comparitor 288 are equal both lines 290 and 292 have no signal thereon and thereby cause both AND gate 342 and 344 to be disabled and thereby provide no further SPP pulses to the X position counter.

If the largest string count register does not receive a count of 20 or greater from the first set of the working areas found, the working area scans continue at each consecutive X position along the blood smear on the slide.

As soon as another good working area is found, the ones are fed into the string register 218 and the first X position of the new string is loaded into X position register 272.

If the string count becomes greater for a subsequent string of consecutive good working areas than the first string of good working areas found, then comparator 232 causes a high signal on line 240 which in combination with the high signal on line 244 at the end of the string found enables AND gate 242 which enables the string count in counter 224 to be loaded into the largest string count register 236 and the position of the start of the present string which is in the X position register 272 to be loaded into the largest string position register 278 thereby replacing the previously found X position.

If the string found is 20 or greater, the largest string decoder 378 causes the output line 382 to be high and thereby initiates the end of the working area scans and positions the X position counter to the desired location for the starting of the classification scanning.

If the string counter 224 never reaches 20 during a working area detector cycle the working area scans ultimately reach the end of the blood smear, and the area shift register 200 has at least three out of four zero bits indicating that three out of four of the last working areas scanned had a red blood cell count of 10,000 or less. The decoder 206 then enables the output line 208 to go high which provides a high signal on line 318 which provides a high input at AND gates 390, 312 and AND gate 316.

When the end of the blood smear is reached and a string of good working areas has been found, but none are greater than 20, the position of the largest string found is used to determine where the optical axis of the scanner is located along the X coordinate of the slide to begin the classification and search modes of the pattern recognition system. If the position of the largest string is greater than 6 mm from the end of the blood smear, then the slide is moved so that the optical axis is disposed within the largest string of good working areas found. If on the other hand, the largest string of good working areas is found at 6 mm or less from the end of the blood smear, then the optical axis of the scanner is disposed 6 mm from the end of the blood smear to start the classification and search scan mode of operation. This is accomplished as set forth hereinafter.

It should be remembered that the X position counter has stored in it at the end of the scan the position at which the last working area was scanned. Since that represents the position of the X coordinate at the end of the blood smear adder 298 produces on output line 300 the difference between the starting position of the largest string and the end of the blood smear. That is, adder 298 receives on line 262 the count in X position counter 256 and from line 296 the compliment of the X position stored in the largest string position register. Adder 298 thus provides the difference between the position of the largest string and the end of the blood smear which is provided to decoder 302 which provides an output on line 304 that is high if the difference is greater than 6 mm and a high signal on line 306 if it is 6 mm or smaller.

Where the difference is greater than 6 mm, output line 304 enables AND gate 390 which has also received a high signal on the input line connected to the output line 376 of the largest string decoder 378. The enabling of AND gate 390 causes OR gate 254 to be enabled which causes the multiplier 348 to provide to adder 284 the product of the count in the largest string count register 236 ×0.2 which is added onto the X position of the largest string count by adder 284 and provided to the comparator 288.

The X position counter is then stepped down until the count in the X position counter is equal to the sum provided on output line 286 of adder 284.

In the event that the position of the largest string found is less than 6 mm from the end of the blood smear the adder 298 has a difference which when decoded by the decoder 302 produces a high signal on line 306. The high signal on line 306 enables OR gate 308 which in turn causes a high signal on line 314 to enable AND gate 316. A high signal is thus produced on line 320. The high signal on ine 320 causes counter 322 to be loaded with the binary representation of 6 mm which is stored in the computer and provided on lines 324 from the computer. The binary representation of 6 mm is used to preset the counter 322. When the SPP pulses start, the counter 322 is stepped down and each SPP pulse causes the AND gate 332 to be enabled. The line 330 from decoder 328 is also high because the count in counter 322 is greater than zero. AND gate 332 is enabled by the high signals on lines 334 and 330 each time an SPP pulse is generated. Each SPP pusle is thus passed to OR gate 338 which steps down the X position counter to a position 6 mm from the end of the blood smear. As soon as the X position counter has been stepped down to a point where it causes the platform to be moved 6 mm, the counter 322 has been stepped to zero and thereby causes the decoder 328 to produce a low signal on line 330 which disables the AND gate 332 and no further SPP pulses aer provided to the X position counter 256 to step it down any further.

There is one other condition for ending the search for a good working area and that is when the end of the blood smear has been reached and no good working area has been found. In such an event the string counter 224 is never stepped and thereby causes the largest string count in register 236 to be zero. When the largest string is zero the largest string decoder 378 provides a low signal on output line 376 which is fed to AND gate 312 and causes AND gate 312 to be enabled when the end of the blood smear is reached. The enabling of AND gate 312 causes OR gate 308 to be enabled which in turn enables AND gate 316 which has also received a high input signal on input line 318. A high signal on output line 320 causes the binary representation of 6 mm to be preset into the counter 322. When the SPP pulses start, the counter 322 is stepped down until such time as the X position counter has been stepped down to a count which causes the platform to be moved 6mm from the end of the smear with respect to the optical axis of the scanning means.

It can therefore be seen that the working area detector allows the selection of the working area in accordance with the following conditions:

1. When a string of good working areas larger than 20 has been found, the position at which the classification scan is started is determined by multiplying the largest string length by 0.2 and adding it to the X coordinate of the start of the string of 20 or greater. The stage is then moved to that position with the blood smear disposed below the optical axis of the scanner at the X coordinate position found.

2. The second method of selecting a working area is used when no string has been found that is 20 or greater and the position of the start of the string of good working areas is greater than 6 mm from the end. When this happens the string length of the longest string is multiplied by 0.2 and this is added to the position of the start of the largest string found and that is the position at which the blood smear is scanned at the start of the classification cycle.

3. A third condition that allows the selection of the working area is when the end of the string is reached and the X position of the largest string is less than 6 mm from the end of the blood smear. In that situation, the position of the blood smear is moved 6 mm from the end of the blood smear and the scanning for classification begins 6 mm from the end in the reverse direction.

4. The fourth condition that allows selection of the working area is the finding of the end of the blood smear with no string stored in which case the blood smear is moved so that the optical axis of the scanner is 6 mm from the end of the blood smear and the classification scan started.

It should be noted that when the first two conditions are found, the slide is moved so that the blood smear is within the largest string round and the classification smear proceeds at the point within the good working area and proceeds from the more dense to the less dense portion of the smear. However, when the third and fourth conditions are found and the slide is moved so that the optical axis is disposed 6mm from the end of the blood smear, the blood classification scans are moved towards the more dense area as the blood smear is scanned.

It can therefore be seen that a new and improved pattern recognition system with working area detection has been provided. The system allows for the variation in blood smears and provides a suitable method for quickly finding an optimum area for scanning the blood smear to facilitate classification.

Moreover, a valuable tool has been provided for determining automatically when the optical scanner is disposed over an area of the blood smear which has approximately 50% of the red blood cells touching. That is, the provision of the perimeter detector and area detector in combination with the counters and area perimeter calculator is a powerful tool for discriminating good working areas having a desired percentage of red blood cells touching from areas which are too densely populated with red blood cells or too sparsely populated with red blood cells.

In addition, the automatic working area detection enables the process of providing a differential white cell count to be completely automated in that the need for operator intervention for starting the search and classification scans in an area which must be searched for by the operator is eliminated.

Moreover, the system incorporates tools for finding an optimum area to begin a search and classification scan, even when an ideal blood smear has not been provided. In this respect while an ideal blood smear would contain at least 20 consecutive good working areas along the X axis of a slide, the instant system provides alternative portions of the slide in which to start a search and classification scan based on the longest string found and the position of the longest string found. In addition, even where no good working area has been found a provision is made for starting the search and classification scan 6mm from the end of the blood smear.

Finally, the system enables flaws and inconsistencies of a blood smear to be substantially ignored in the good working area so that the length of the good working area can be accurately determined.

Without further elaboration the foregoing will so fully illustrate our invention that others may, by applying current or future knowledge, readily adapt the same for use under various conditions of service.

What is claimed as the invention is:

1. In a pattern recognition system for examining patterns, means to enable examination for pattern detection in a good working area, said means including scanning means for scanning a field, means for moving said field with respect to the scanning means to change the position of the field scanned, and detection means responsive to the scanning means for determining when the position of a field scanned is in a good working area, said detection means being responsive to said scanning means to determine the distribution density of patterns at each different position at which a field is scanned, said moving means responsive to said detection means for moving the position of said field with respect to said scanning means so that a first position at which a field is examined for pattern detection is in a good working area having a predetermined distribution density of patterns.

2. In a pattern recognition system for examining a blood smear on a slide, means to enable examination for pattern detection in a good working area, said means including scanning means for scanning a field, means for moving said field with respect to the scanning means to change the position of the field scanned, and detection means responsive to the scanning means for determining when a field scanned is in a good working area, said moving means responsive to said detection means for moving said field with respect to said scanning means so that a first position of said field examined for pattern detection is in a good working area, said blood smear having a good working area in the portion of said smear wherein 50% or less of red blood cells are touching.

3. In a pattern recognition system for examining a blood smear on a slide, means to enable examination for pattern detection in a good working area, said means including scanning means for scanning a field, means for moving said field with respect to the scanning means to change the position of the field scanned, and detection means responsive to the scanning means for determining when a field scanned is in a good working area, said moving means responsive to said detection means for moving said field with respect to said scanning means so that a first position of said field examined for pattern detection is in a good working area, said detection means including means for sampling a plurality of points in each position of said field which is scanned, area means for counting the number of said plurality of points sampled in said field which fall on a red blood cell and perimeter means for determining the number of said plurality of points on the field which fall on the perimeter of a red blood cell and calculations means for providing a ratio of the counts of said area means to said perimeter means.

4. The pattern recognition system of claim 3 wherein said means for moving said field with respect to said scanning means moves said slide so that consecutive fields along the length of the blood smear are scanned, said calculation means providing a ratio of the counts of said area means to said perimeter means for each consecutive field scanned.

5. The pattern recognition system of claim 4 wherein said slide is disposed in a predetermined position prior to the first scan, means responsive to said calculation means so that after the first scan has been made it controls the direction of said means for moving said field in accordance with the ratio produced by said calculation means, said means responsive to said calculation means causing said means for moving said field to move said field backward with respect to said scanning means unless a predetermined ratio from said calculator has been reached or a predetermined position on said slide has been reached whereupon said means for moving is caused to move said smear forward with respect to said scanning means after each field has been scanned.

6. The pattern recognition system of claim 5 wherein means are provided responsive to said calculation means for determining a predetermined ratio representative of a good working area having been scanned, and second counting means for counting the number of times that a predetermined ratio representative of a good working area has been found.

7. The pattern recognition system of claim 6 wherein said second counting means counts the number of consecutive fields scanned having a good working area and position storage means are provided for storing the location of the start of the string of good working areas.

8. The pattern recognition system of claim 7 wherein said means for moving said smear with respect to said scanning means continues to move said blood smear until either a string of a predetermined size of good working areas has been found or the end of the blood smear has been found.

9. The pattern recognition system of claim 8 wherein detection means are provided for determining the size of the largest string of fields in consecutive good working areas found until said string of a predetermined size of good working areas is found and a largest string position storage means is provided for storing the position where the largest string of fields with a good working area have been found.

10. The pattern recognition system of claim 9 wherein the moving means is operative at the end of the working area scanned to move the field with respect to the scanning means so that the scanning means is located at the position of said field representated by the position stored in said largest string position storage means.

11. The pattern recognition system of claim 10 wherein said moving means is responsive to the end of the consecutive scans to move the scanning means to a predetermined distance from the end of the blood smear if the largest string of good working areas found is within said predetermined distance from the end of the blood smear or no good working areas have been found.

12. In a pattern recognition system for examining patterns on a field, scanning means for sampling a plurality of points in said field and generating signals in accordance with the colors in said field at said plurality of points, said system being characterized by area means responsive to said signals for counting the number of points lying on said patterns in said field to produce an area count and perimeter means responsive to said signals for counting the number of points lying on the edge of said patterns in said field to produce a perimeter count and calculation means responsive to said area means and perimeter means for producing a ratio of the area count to the perimeter count to enable the determination of a suitable position on said field to examine said patterns in said field based on the location at which is found a predetermined ratio of area count to perimeter count.

13. The pattern recognition system of claim 12 wherein said pattern recognition system examines a blood smear on a slide and said area means counts the number of points lying on red blood cells and said perimeter means counts the number of points lying on the perimeter of a red cell.

14. A method of recognizing a smear comprising the steps of;
(a) positioning a slide held on a movable stage of a microscope to a predetermined position such that the test smear on said slide is positioned within a view field of said microscope,
(b) moving said stage along said smear in response to an instruction from a control unit such that different areas of said test smear along the length of said smear are sequentially positioned within the view field of said microscope.
(c) sequentially detecting by a detector objects to be counted in test samples at respective measuring points appearing in the view field of said microscope as said stage is moved, to determine distribution densities of the objects to be counted at the respective measuring points,
(d) comparing the distribution densities at the respective measuring points with a preset distribution density to determine an optimum test area on the test smear, and
(e) moving said stage in response to an instruction from said control unit such that the view field of said microscope is positioned to said optimum test area.

15. A method for recognizing a smear according to claim 14 wherein in said step (b) a high object distribution density area of said smear is first positioned to the view field of said microscope and the measuring point is sequentially moved toward a low object distribution density area.

16. A method for recognizing a smear according to claim 14 or 15 wherein said test sample is blood smeared on said slide along a longer side of said slide.

17. A method for recognizing a smear according to claim 16 wherein said objects to be counted are red blood corpuscles and said objects to be recognized are white blood corpuscles.

* * * * *